United States Patent [19] [11] Patent Number: 4,532,935
Wang [45] Date of Patent: Aug. 6, 1985

[54] BRONCHOSCOPIC NEEDLE ASSEMBLY

[76] Inventor: Ko P. Wang, 813 Jamieson Rd., Lutherville, Md. 21093

[21] Appl. No.: 472,603

[22] Filed: Mar. 7, 1983

Related U.S. Application Data

[63] Continuation-in-part of Ser. No. 438,245, Nov. 1, 1982, which is a continuation-in-part of Ser. No. 260,602, May 6, 1981, abandoned.

[51] Int. Cl.$^3$ .................... A61B 10/00; A61M 5/00
[52] U.S. Cl. .................... 128/753; 128/347; 128/754; 128/348.1; 604/121
[58] Field of Search ............... 128/348.1, 343, 763, 128/356, 754, 752–753; 604/121, 128, 159, 161, 162, 164–166, 169, 170–171, 187–188, 220, 158, 160, 163, 166–167, 272–273, 264, 51, 53, 181, 218, 95

[56] References Cited

U.S. PATENT DOCUMENTS

| 2,623,521 | 12/1952 | Shaw | 128/754 |
| 3,438,373 | 4/1969 | Pannier, Jr. | 128/214.4 |
| 3,500,828 | 3/1970 | Podhora | 128/214.4 |
| 3,537,451 | 11/1970 | Beck | 128/214.4 |
| 3,598,108 | 8/1971 | Jamshidi et al. | 128/754 |
| 3,659,610 | 5/1972 | Cimber | 604/162 |
| 3,727,602 | 4/1973 | Hyden et al. | 128/753 |
| 3,747,812 | 7/1973 | Karman et al. | 604/220 |
| 3,855,561 | 5/1975 | Cami | 128/214 |
| 3,866,609 | 2/1975 | Sparks | 128/303 R |
| 3,993,079 | 11/1976 | Gatztanondo | 128/347 |
| 4,006,744 | 2/1977 | Steer | 128/214.4 |
| 4,007,732 | 2/1977 | Kuaule et al. | 128/754 |
| 4,041,936 | 8/1977 | Carden | 128/6 |
| 4,052,989 | 10/1977 | Kline | 128/349 R |
| 4,073,297 | 2/1978 | Kopp | 128/214.4 |
| 4,096,860 | 6/1978 | McLanghlin | 128/214.4 |
| 4,159,022 | 6/1979 | Peusner | 604/159 |
| 4,181,132 | 1/1980 | Parks | 128/399 |
| 4,230,123 | 10/1980 | Hawkins, Jr. | 128/754 |
| 4,249,541 | 2/1981 | Pratt | 128/753 |

FOREIGN PATENT DOCUMENTS

193900 3/1923 United Kingdom ............ 128/347

Primary Examiner—C. Fred Rosenbaum
Assistant Examiner—Gene B. Kartchner
Attorney, Agent, or Firm—Cushman, Darby & Cushman

[57] ABSTRACT

A completely flexible bronchoscopic needle assembly having fixed and retractable needle embodiments for use with a fiberoptic bronchoscope.

13 Claims, 15 Drawing Figures

BRONCHOSCOPIC NEEDLE ASSEMBLY

RELATED APPLICATIONS

This application is a continuation-in-part of my copending U.S. Application Ser. No. 438,245 filed Nov. 1, 1982 entitled "Bronchoscopic Needle Assembly" which, in turn, is a continuation-in-part of my copending U.S. Application Ser. No. 260,602 filed May 6, 1981, now abandoned, entitled "Bronchoscopic Needle", the disclosures of each being expressly and fully incorporated hereinto by reference.

BACKGROUND AND SUMMARY OF THE PRESENT INVENTION

In my copending application Ser. No. 260,602, a completely flexible bronchoscopic needle is disclosed wherein relatively non-invasive biopsy procedures can be performed utilizing the needle in combination with a fiberoptic bronchoscope. The attending physician inserts the bronchoscope into a predetermined one of the patient's natural orifices depending upon the particular organ desired to be biopsied. Thereafter, the needle assembly in accordance with the invention of Ser. No. 260,602 is slideably inserted into a receiving passageway of the bronchoscope. The needle is urged into the tissue of the patient by a stabbing force exerted on the proximal end thereof (e.g. the end on the exterior of the patient's body) after the tubular needle portion comes into the bronchoscope's field of view. The bronchoscope enables the attending physician to accurately position the needle and to penetrate the exact location of the desired organ due to the viewing capabilities provided thereby. The present application is directed to improvements on the needle assembly disclosed in my copending application Ser. No. 260,602.

Heretofore, when biopsies were desired to be taken of the lymph nodes, for example, so as to aid in the diagnosis of carcinoma, the prior techniques would all typically utilize a substantially rigid needle and penetrate the body via percutaneous entry. For example, U.S. Pat. Nos. 3,630,192 and 3,628,524 each to Jamshidi disclose prior art biopsy needles suitable for percutaneous entry. U.S. Pat. No. 4,249,541 to Pratt discloses that a flexible biopsy instrument can be utilized in combination with a fiberoptic bronchoscope. However, Pratt's needle does not provide any locking means at the distal end thereof so that the needle may have a tendency to resist penetration of the desired tissue; e.g. the needle may retract somewhat into the bronchoscope passageway.

The needle assembly according to the present invention, however, solves such deficiencies by not only providing suitable protecting means which can at the desired time be removed to expose the sharp edge of the tubular needle so as to permit taking of biopsy samples but also ensures that the sharp needle will not resist penetration in to the tissue.

A particular problem in utilizing completely flexible bronchoscopic needles is to ensure that the rigid tubular needle (typically only about 2-3 cm in length) remains attached to the distal end of the needle assembly. Since the needle will penetrate the bronchial walls to access the lymph nodes or hard tumors therebehind, for example, there exists the possibility that upon withdrawal of the needle, the tubular needle portion will become totally separated from the assembly and remain lodged in the tissue. This would, of course, be a disastrous occurrence. Retrieval of the separated needle may be doubtful and would require the highest surgical skill. The present invention specifically addresses such a problem by providing a secure metal tip in the distal end of the catheter to which the needle is securely attached.

Furthermore, according to one embodiment of the present invention, the protective functions briefly mentioned above are realized by providing a tubular needle which is fully retractable within the outer catheter of the assembly, the smooth-shouldered distal end of the catheter thereby protecting both the fiberoptic bronchoscope and the patient from inadvertent needle damage. Thus, when it is desired to take a biopsy tissue sample, the retracted needle need only be extended beyond the distal end of the catheter. As previously noted, bronchial wall or hard tumor tissue will need to be penetrated and thus may present certain resistance to the needle. It is highly undesirable for the needle to inadvertently retract inside the catheter due to such resistance as this would not enable the attending physician to accomplish the desired organ biopsy. However, according to the present invention, secure locking engagement can be established so as to prevent inadvertent retraction of the needle into the catheter.

The above specifically noted advantages of the present invention and others will become more clear after careful consideration is given the detailed description of the preferred exemplary embodiments thereof which follows.

BRIEF DESCRIPTION OF THE ACCOMPANYING DRAWINGS

Reference will be hereinafter made to the accompanying drawings wherein like reference numerals throughout the various figures denote like structural elements and wherein.

DETAILED DESCRIPTION OF THE PREFERRED EXEMPLARY EMBODIMENTS

The present invention generally includes two embodiments hereinafter referred to as the fixed needle embodiment and the retractable needle embodiment and can be further subdivided into Types I, II, III, IV and V, as will be discussed in greater detail below.

Figures 1, 2, 3, 4:
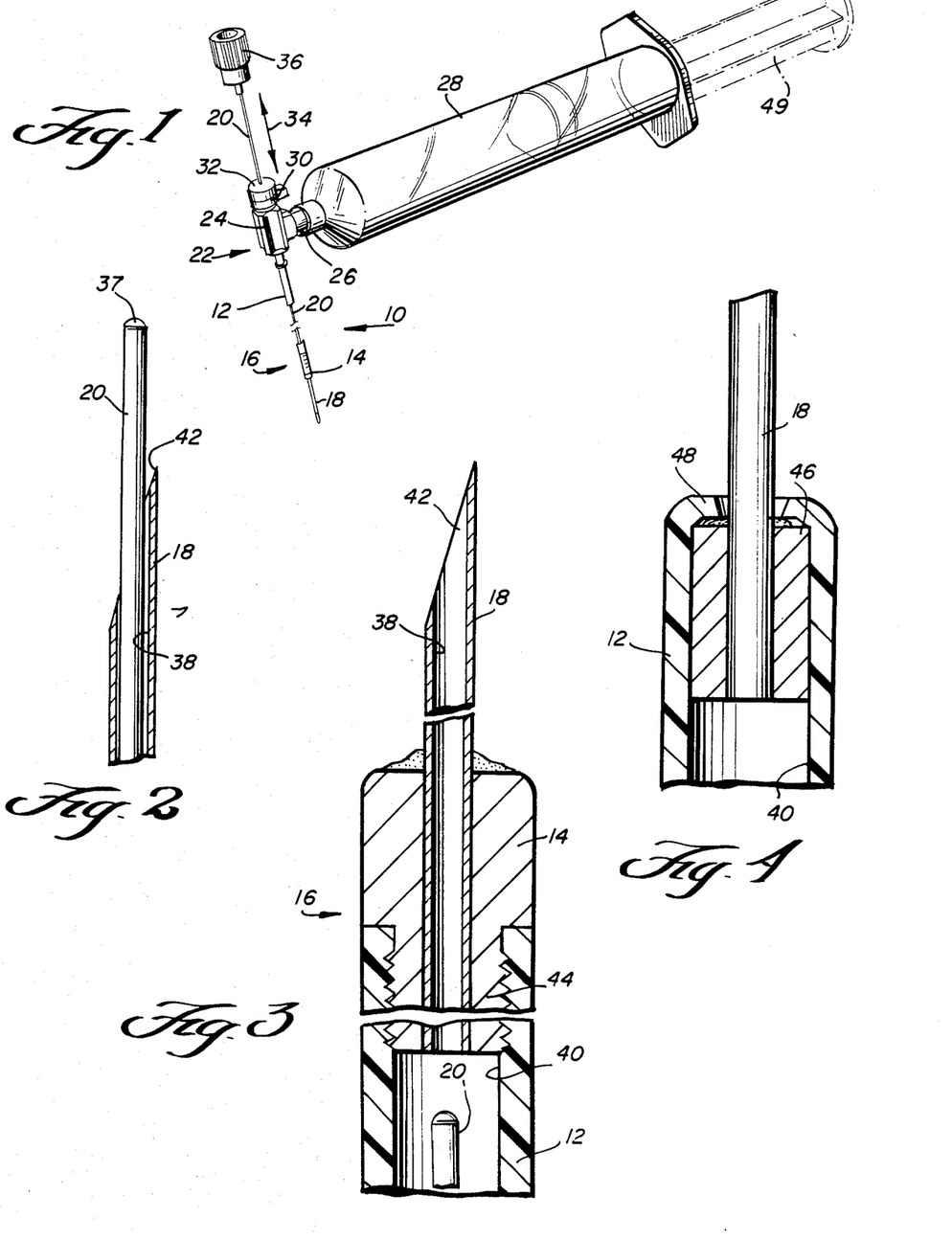
FIG. 1 is a representative perspective view of the biopsy needle assembly in accordance with the present invention.
FIG. 2 is a detailed cross-sectional view of one type of the fixed needle embodiment of the present invention particularly showing the protective stylet in extension.
FIG. 3 is a detailed cross-sectional view of the distal end of one type of the fixed needle embodiment of the present invention.
FIG. 4 is a detailed cross-sectional view of the distal end of an alternative means for fixing the needle in accordance with the FIG. 3 embodiment.

FIG. 1, however, is representative of the primary embodiments of the present invention and the reader may wish to periodically refer thereto for an overall view of the present invention. As shown in FIG. 1, the biopsy needle assembly 10 generally includes an outer catheter 12, a metal slip tip 14 fixed to the distal end of catheter 12, and a rigid hollow needle 18 coaxial with tip 14. A flexible stylet 20 is slideably received with catheter 12 for a purpose which will become more clear from the discussion below.

The proximal end 22 of assembly 10 preferably includes a conventional two-directional leur lock 24, one of the directional nipples 26 for accepting an aspirating device, such as, a conventional syringe 28, the other directional nipple 30 being coaxially positioned relative to catheter 12. Covering nipple 30, I prefer to utilize an elastomeric seal 32 through which stylet 20 passes. Seal 32 is provided so as to permit all suction forces generated by syringe 28 to be communicated through needle 18 when it is desired to obtain biopsy tissue samples. Thus, no leakage will occur in the vicinity of stylet 20 where it passes through seal 32 yet reciprocal movement (arrow 34) of stylet 20 is permitted. A grippable cap 36 is fixed to the proximal end of stylet 20 so as to permit the attending physician to effect such reciprocal movement.

The reader should bear in mind that the needle assembly of the present invention is particularly well suited for use in combination with a flexible fiberoptic bronchoscope, and thus, must itself be completely flexible. As used herein and in the appended claims, the term "flexible" is meant to refer to axial flexion through an arc of 360° (e.g. axially looped). Thus, such flexibility permits the needle assembly to negotiate sharp turns even to the extent of permitting U-turns thereof.

In order to permit such flexibility I prefer to construct catheter 12 of a durable plastic material. Similarly, stylet 20 can be constructed of fine gauge metal or plastic wire, the flexibility thereof being substantially equal to the flexibility of the catheter 12 in which it is slideably received.

1. Fixed Needle Embodiment—Type 1 (FIGS. 2-4)

With the above noted generalities regarding the biopsy needle assembly 10 in mind, attention will now be directed to FIGS. 2-4 wherein one embodiment thereof (e.g. the Type I needle) will be described in greater detail.

Stylet 20 is of sufficient length so that the smoothly rounded distal end 37 will extend beyond the sharp edge 42 of needle 18 (see FIG. 2). Preferably, stylet 20 extends about 1 to 3 cm beyond the sharp edge 42 of needle 18. In such a manner, the smoothly rounded end 37 of stylet 20 will protect the bronchoscope and the patient from inadvertent damage due to needle 18 during insertion of assembly 10. Once needle 18 is in the vicinity of the tissue area to be biopsied, stylet 20 is withdrawn so that end 37 is housed in hollow 38 of needle 18 thereby exposing sharp edge 42.

The diameter of stylet 20 is chosen so as to be closely fitted within needle cavity 38. While the structures of the present have been shown in a greatly exaggerated scale for clarity of presentation, the reader should realize that the needle 18 and stylet 20 are very small gauge. Thus, for all intents and purposes, the transition between the sharp edge 42 of needle 18 and the exterior surface of stylet 20 is substantially smooth when the latter is extended for protective functions.

FIG. 3 represents a detailed cross-sectional view of the distal end 16 of the fixed needle (Type I) embodiment of the present invention. As shown, tubular needle 18 defines needle cavity 38 in communication with interior cavity 40 of catheter 12. Interior cavity 40 is preferably substantially cylindrical throughout its entire length. Needle cavity 38 is coaxially situated with interior cavity 40, the diameter of the former being preferably about one-third to about one-half that of the latter. Stylet 20, on the other hand, is sized so as to be closely received within needle cavity 18. Thus, stylet 20 is similarly about one-third to about one-half the diameter of interior cavity 12 so as to establish a significant annular space through which biopsy tissue and/or fluids can easily flow.

Needle 18 at its distal end defines a sharp edge 42 for penetrating a patient's tissue to obtain samples thereof while the proximal end of needle 18 is rigidly fixed in tip 14. Needle 18 and tip 14 can be fixed to one another utilizing suitable solders, adhesives or like bonding agents, or alternatively, needle 18 can be integrally formed with tip 14.

Tip 14 is an important feature of the present invention in that it effects secure union between needle 18 and catheter 12 thereby preventing deleterious separation thereof. Tip 14 is preferably constructed of a hard metal (e.g. stainless steel) or hard plastic material.

In accordance with the embodiment of FIG. 3, tip 14 is provided with a male threaded member 44 so that when threadingly inserted into interior cavity 40, the male threads on member 44 act as a tapping tool to cut corresponding female threads into catheter 12. Therefore, a self-tapping system is established whereby axial forces will be resisted thereby preventing separation of tip 14, and thus needle 18, from catheter 12.

A second embodiment of the distal end 16 of the fixed needle (Type I) embodiment is depicted in FIG. 4. In the FIG. 4 embodiment, tip 46 is similarly rigidly fixed to needle 18. However, in order to resist axial forces, I prefer to dimension the exterior diameter of tip 46 slightly larger than the diameter of interior cavity 40 so that a secure, press-fitting relationship is established. The terminal end of catheter 12 may then be heat-formed so that upon cooling, the distal end of catheter 12 is formed with an inward flange 48 thereby at least partially closing interior cavity 40 over tip 46. In order to effect such closure, tip 46 must be recessed within cavity 40. Thus, partial closure of the distal end of catheter 12 will resist axial forces in a direction tending to separate needle 18 from catheter 12 while the press-fitting relationship between tip 46 and catheter 12 resists axial forces in a direction tending to push needle 18 into cavity 40.

In practice, the needle assembly 10 having the fixed needle embodiment of the present invention is inserted into the flexible fiberoptic bronchoscope with stylet 20 extended beyond sharp edge 42 so as to provide protective functions. When the desired tissue area is located, stylet 20 is withdrawn to a position below sharp edge 42 and the needle 18 is penetrated into the tissue area by a stabbing motion. When the biopsy material is desired to be withdrawn, plunger 49 of syringe 28 is pulled thereby creating a significant suction force. Since stylet 20 is sized so as to be closely fitted within hollow 38 of needle 18, the biopsy material will not pass therethrough when stylet 20 is housed with hollow 38. However, when stylet 20 is withdrawn completely from hollow 38, a significant space is provided with enables biopsy material to flow therethrough due to the suction force and be deposited into syringe 28. Thereafter, the biopsy material can be examined for diagnostic purposes.

A significant advantage of utilizing the fixed needle embodiment of the present invention is that stylet 20 need not be completely removed from catheter 12 so as to permit aspiration. Thus, merely withdrawing stylet 20 so that end 37 is about 1-2 cm interiorly removed from hollow 38 will permit the biopsy tissue and/or fluids to flow therearound in the annular space.

2. Retractable Needle Embodiment—Type II (FIGS. 5-8)

Once again the reader is directed to the general discussion regarding assembly 10 as noted above with reference to FIG. 1. Such general structures previously noted can be modified in accordance with a second retractable needle embodiment (e.g. Type II embodiment) of the present, which embodiment will now be described in greater detail with reference to accompanying FIGS. 5-8.

The distal end 16 of the Type II retractable needle embodiment (see FIGS. 5 and 7) includes a tip 100 threadably coupled to outer catheter 101 in a manner similar to that described above with reference to tip 14 and catheter 12 in FIG. 2. However, needle 102 (defining needle cavity 104) is not fixed to tip 100, but rather is reciprocably moveable therein. Needle 102 is fixed to and carried with inner catheter 106 while stylet 108 is slideably received in inner catheter 106.

The proximal end 22 of assembly 10 in accordance with the Type II needle embodiment (see FIGS. 6 and 8) preferably includes an outer catheter cap 110 fixed to outer catheter 101, an inner catheter cap 112 fixed to inner catheter 106, and a stylet cap 114 fixed to stylet 108. In such a manner, independent reciprocal movement of inner catheter 106 and stylet 108 relative outer catheter 101 is achieved. Mutual locking of caps 110, 112 and 114 can be provided by conventional threading engagement of male threads 116 and 118 on caps 110 and 112, respectively, with cooperating female threads 120 and 122 defined on caps 112 and 114, respectively.

Preferably, a conventional two-directional leur lock 30 having an elastomeric plug 121 (see FIG. 8) can be provided intermediate caps 112 and 114 to permit similar aspirating functions as previously described with reference to assembly 10 depicted in FIG. 1. In the retractable needle embodiment, however, aspiration is effected through the cavity of inner catheter 106 with stylet 108 completely removed, or alternatively, the inner catheter 106 can be sized so as to define an annular space with stylet 108 through which biopsy material can flow.

Figure 5:
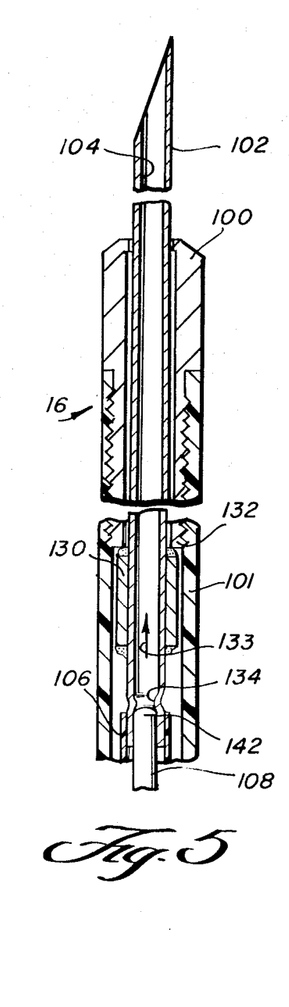
FIG. 5 is a detailed cross-sectional view of the distal end of one type of the retractable needle embodiment of the present invention.

An important feature of the Tyep II needle embodiment of the present invention is that means are provided for maintaining a biasing force on needle 102 so as to resist compression forces tending to retract needle 102 into catheter 101. Such means are extremely important when consideration is given to the fact that oftentimes relatively tough tissue must be penetrated (e.g. bronchial walls or hard tumors) in order to obtain the desired biopsy material. Thus, such tough tissue may exert a sufficient amount of resistance against needle 102 so as to cause at least partial retraction thereof into outer catheter 101. Such partial retraction of needle 102 is to be strictly avoided. For example, should partial retraction occur, the attending physician will not be able to completely penetrate the bronchial wall in order to obtain a biopsy sample of the lymph nodes therebehind. This may lead to a misdiagnosis of the patient's ailment, for example, as the tissue sample which will be obtained will not be of the diseased lymph node, but rather will be of the undiseased bronchial wall.

In order to prevent such occurrences, I prefer to provide needle 102 with a fixed hub 130 which acts as a limit member to limit the extended travel of needle 102. The limiting functions of hub 130 are achieved by ensuring that it bears against the proximal end 132 of tip 100 and thus hub 130 should also be constructed of a hard material, such as, stainless steel or the like.

To ensure that hub 130 securely bears against the proximal end 132 of tip 100, a biasing force (arrow 133) is applied by stylet 108 acting against recessed surfaces 134 formed in needle 102. Recessed surfaces 134 are preferably formed merely by crimping a predetermined portion of needle 102 so as to reduce the diameter of needle cavity 104 at such portion yet will still be of sufficient diameter to permit biopsy material to pass therethrough. Alternatively, integral stop members could be formed at a predetermined location in needle cavity 104 or a flange could be provided on the distal end of stylet 108.

The magnitude of biasing force 133 is determined by providing stylet 108 with sufficient axial length so that it is longer (on the order of about 1 to about 3 cm) than the axial length of assembly 10 as measured between recessed surfaces 134 and the proximal end of assembly 10. Thus, upon first contact of the rounded distal end 142 of stylet 108 with recessed surfaces 134, a predetermined excess of stylet 108 will be apparent at the proximal end of assembly 10. Upon removal of such excess by forcing cap 114 in a direction towards distal end 16, a biasing force of sufficient magnitude will be exerted against needle 102 to ensure that hub 130 bears against proximal end 132 of tip 100 thereby establishing rigid extension of needle 102 to prevent undesired retraction thereof.

Figure 6:
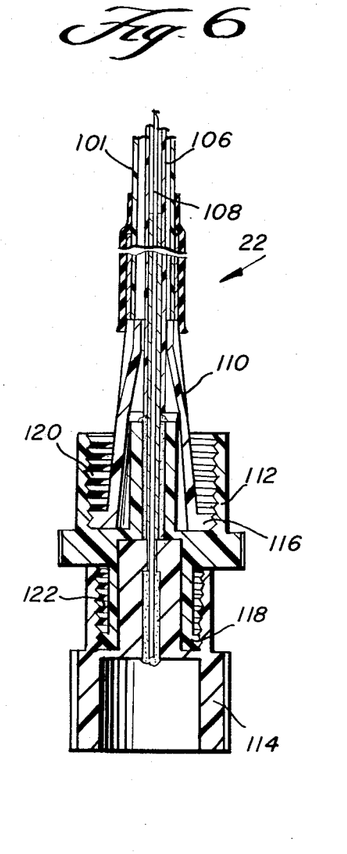
FIG. 6 is a detailed cross-sectional view of the proximal end of the FIG. 5 embodiment.
Figure 7:
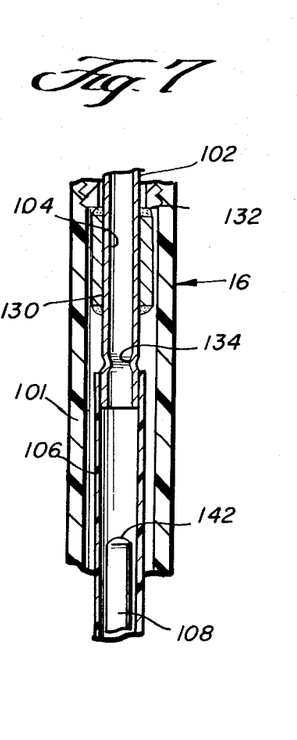
FIG. 7 is a detailed view similar to FIG. 5 showing the stylet partially retracted from the tubular needle.
Figure 8:
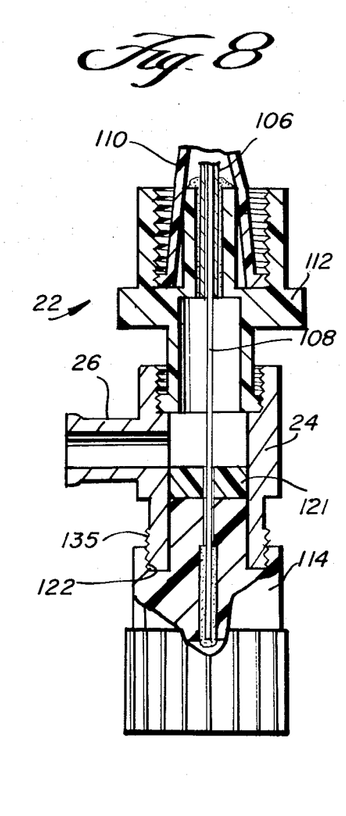
FIG. 8 is a detailed view of another embodiment of the proximal end of the FIG. 5 embodiment showing in particular a leur lock in combination therewith.

Secure locking engagement between threads 118 and 122 of caps 112 and 114, respectively, maintaining biasing force (arrow 133) without requiring manual retention of the attending physician. Similarly, threads 135 on leur lock 24 can be provided, if utilized, to maintain the biasing force, threads 135 thereby cooperating with threads 122 of cap 114.

Of course, when desired, needle 102 may be simply retracted by removing such biasing force and retracting inner catheter 106 thereby carrying needle 102 along with it. In such a manner, the bronchoscope and patient can be protected by inserting assembly 10 having needle 102 in a retracted position, yet will enable the attending physician to perform the required biopsy with needle 102 in the securely extended position as previously noted.

3. Fixed Needle Embodiment—Type III (FIGS. 9-10)

Figure 9:
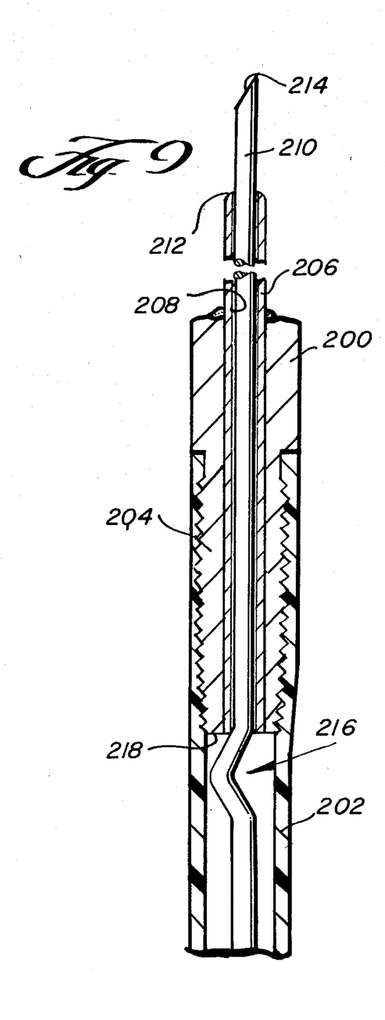
FIG. 9 is a detailed cross-sectional view of another type of fixed needle embodiment in accordance with the present invention.
Figures 10, 11, 12:
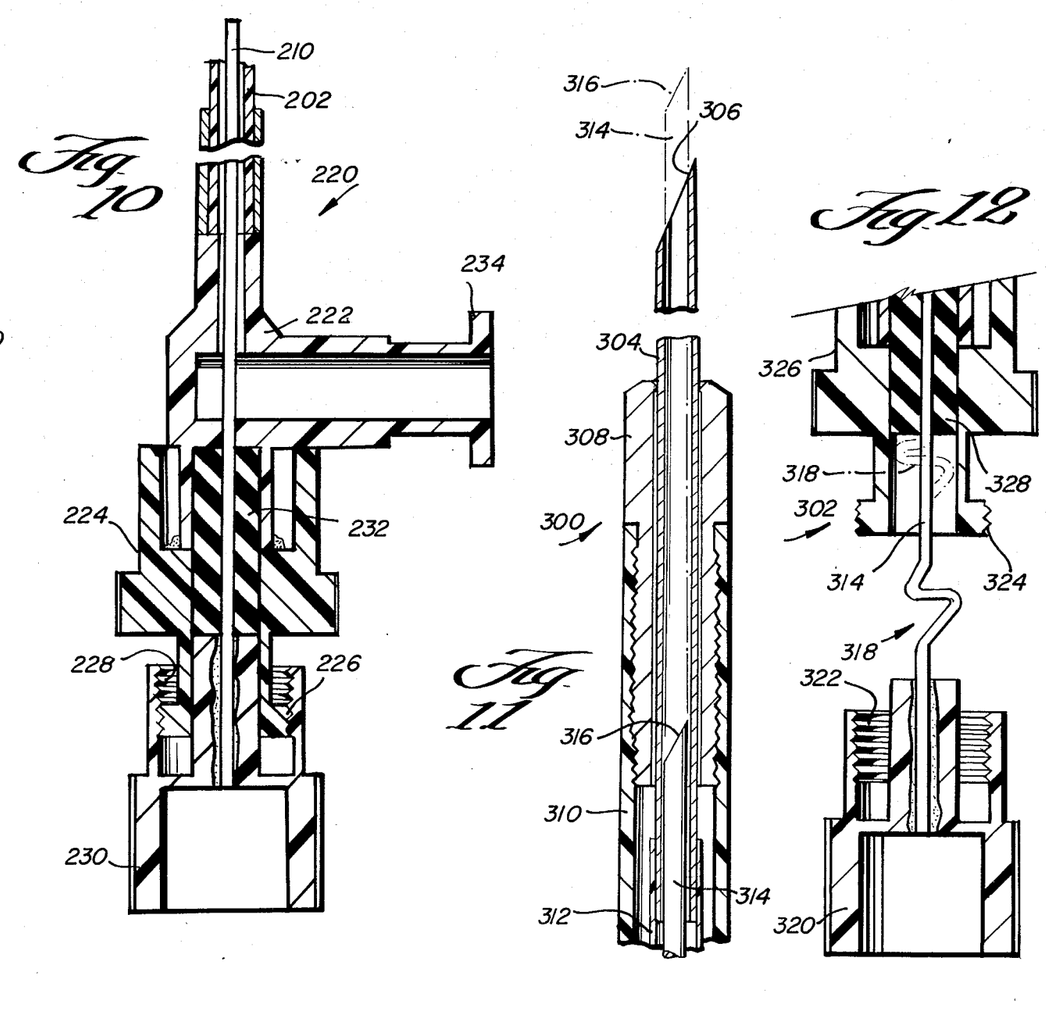
FIG. 10 is a detailed cross-sectional view of the distal end of the FIG. 9 needle.
FIG. 11 is a detailed cross-sectional view of another type of retractable needle embodiment in accordance with the present invention.
FIG. 12 is a detailed cross-sectional view of the distal end of the FIG. 11 needle.

Another type of the fixed needle embodiment (Type III) is shown in FIGS. 9 and 10. It will be readily apparent that the distal end (see FIG. 9) of the Type III embodiment is similar to the distal end of the Type I embodiment in that a metal or hard tip 200 is threadably secured into catheter 202 via male threaded portion 204. Once again, the threaded portion 204 securely attaches tip 200 to catheter 202 so as to prevent withdrawal therefrom.

Rigid tubular needle 206 is fixed to or integral with tip 200, as hereinbefore described, and defines an axial cavity 208 in which stylet 210 is reciprocably moveable. However, the Type III needle utilizes rounded shoulders 212 on the distal end of needle 206 and a sharp beveled edge 214 on the distal end of stylet 210. Thus, with stylet 210 withdrawn into cavity 208, the rounded shoulders 212 of needle 206 serve the protective functions described above. However, when the physician is desirous of penetrating tissue to obtain a sample thereof, stylet 210 is advanced and the beveled edge 214 permits entry into the desired tissue area.

The Type III needle is particularly advantageous since the beveled edge 214 need only extend a minimal distance beyond rounded shoulder 212 (e.g. on the order of about 1 cm) so as to accomplish its tissue penetrating functions. Additionally, once the tissue area has been lanced by virtue of beveled edge 214, the needle 206 can be advanced into the lanced area for sampling and thus stylet 210 can be withdrawn, it having served its intended function.

So as to ensure that beveled edge 214 resists any axial forces tending to withdraw it into cavity 208, I prefer to establish an outward biasing force thereon by virtue of a spring area 216. Spring area 216 also serves as a limit member to limit the advance of beveled edge 214 beyond the distal end of needle 206 since it is not capable of entering cavity 208. Thus, a portion of spring area 216 will bear against the proximal end 28 of tip 200 to prevent further advance of stylet 210. Once such contact is made between spring area 216 and end 218, an excess length of stylet 210 will be apparent at the distal end of the needle assembly. Thus upon further advance of the excess stylet 210, spring area 216 will be flexed and provide the desired biasing force to ensure rigidity of beveled edge 214 beyond shoulders 212 and thus to resist axial forces tending to retract beveled edge 214 into cavity 208.

The proximal end 220 of the Type III embodiment (see FIG. 10) preferably includes a two-directional Leur lock 222 modified by fixing member 224 so as to be coaxial to catheter 202. Member 224 includes male threads 226 so as to be lockably engageable with female threads 228 defined in cap 230. Cap 230 is fixed to the proximal end of stylet 210 so as to permit the physician to grasp same and reciprocably manipulate stylet 210 in catheter 202 as desired.

An elastomeric seal 232 is provided in member 224 so as to be sealingly engaged with stylet 210 yet still permit sliding reciprocal movement thereof. Thus, when an aspirating device, for example, a syringe 28 (see FIG. 1), is attached to nipple 234 of Leur lock 222 and the distal end of stylet 210 is withdrawn from needle cavity 208, biopsy material will be able to flow in the annular space between stylet 210 and the inner walls of catheter 202 under aspiration so that biopsy tissue samples can be obtained for diagnosis. The seal 232 therefore ensures that all suction from the aspirating device will be directed to the distal end of needle 206 to maximize recovery of the biopsy tissue samples.

4. Retractable Needle Embodiment—Type IV (FIGS. 11-12)

The distal end 300 and proximal end 302 of the Type IV retractable needle embodiment of the present invention are shown in accompanying FIGS. 11 and 12, respectively.

The Type IV retractable needle embodiment is substantially similar to the embodiment of e.g. FIG. 5 in that a tubular rigid needle 304 having a sharp distal end 306 is slideably received in tip 308 and outer catheter 310. Inner catheter 312 is attached to needle 304 so as to permit retraction thereof in tip 308 and outer catheter 310 in manner already described above. However, in accordance with this embodiment, stylet 314 which is slideably and reciprocably received in inner catheter 312 includes a sharp cutting edge 316 on the distal end thereof to further aid the physician in penetrating hard tumors or the like. Thus, both the stylet 314 and needle 304 need to be withdrawn in tip 308 to achieve the protective functions thereof already described above. However, when penetration of tissue is desired, the stylet 314 is extended to a position shown in phantom line in FIG. 11. Thereafter it can be advanced into the desired tissue by a stabbing motion.

To ensure initial tissue insertion rigidity of stylet 314, I prefer to include a biasing spring 318 in a portion of the proximal end thereof (see FIG. 12). Thus, when cap 320 and stylet 314 are advanced so as to lockably engage threads 322 with threads 324, the spring 318 in stylet 314 will seat against a portion of member 326 (e.g. seal 328 as shown in FIG. 12) so that inward flexing of spring 318 will occur to thereby bias the distal end of stylet 314 in a direction tending to resist axial compressive forces thereon. This latter biasing position of spring 318 is shown in phantom line in FIG. 12. It should be noted that proximal biasing spring 318 can also be advantageously utilized with any of the embodiments described above.

5. Syringe Needle Assembly—Type V (FIGS. 13-15)

A preferred assembly of the present invention particularly well suited for the Type I and Type III fixed needle embodiments described above is shown in accompanying FIGS. 13-15. Although a smoothly rounded stylet and sharp-edged needle (e.g. Type I fixed needle embodiment) is shown in FIGS. 11-15, the reader should appreciate that the assembly to be described below is similarly applicable for a sharp-edged stylet and smoothly rounded needle (e.g. Type III) fixed needle embodiment.

Figure 13:
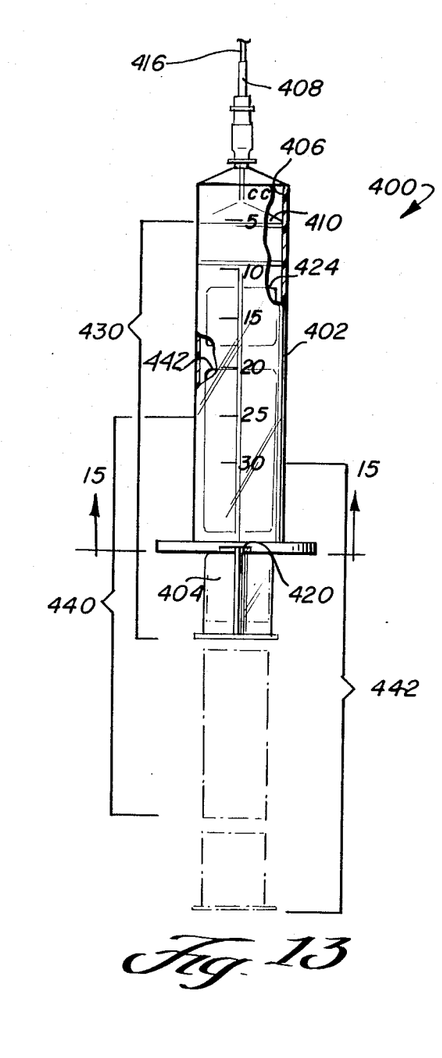
FIG. 13 is an elevational view of the proximal end of another type of needle assembly in accordance with the present invention.
Figure 14:
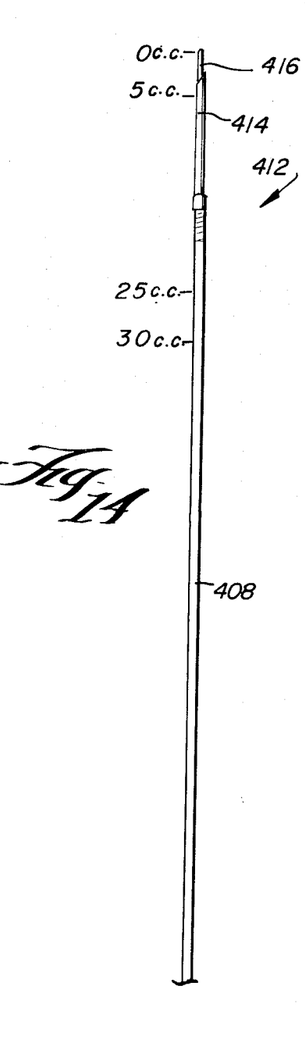
FIG. 14 is an elevational view of the distal end of the FIG. 13 needle.
Figure 15:
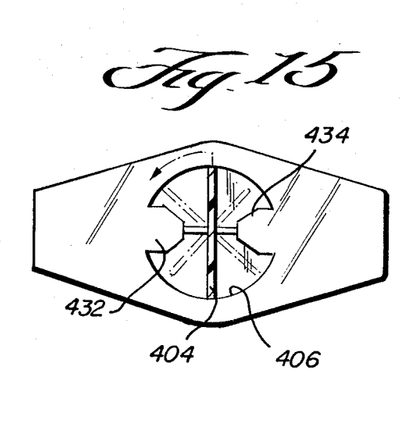
FIG. 15 is a cross-sectional plan view taken along line 15—15 in FIG. 13.

Referring specifically to FIGS. 13 and 14, it can seen that the distal end 400 includes a syringe body 402 in which a plunger 404 is slideably reciprocably moveable. Body 402 defines a cylindrical cavity 406 (see FIG. 15) and is attached to catheter 408 so that the former communicates with the interior cavity defined by the latter. A plunger seal 410 is provided on the distal end of plunger 404 so that upon withdrawal of plunger 404, a suction force is established to encourage biopsy material to flow through catheter 408 and be deposited in cavity 406.

The distal end 412 includes a tubular rigid needle 414 in which stylet 416 is reciprocably moveable in a manner similar to that already described above. However, according to this assembly, the proximal end of stylet 416 is attached to plunger 404 so that upon reciprocal manipulation of the latter, the former will responsively be reciprocably manipulated. This feature of the Type V assembly permits the attending physician to simultaneously manipulate stylet 416 and plunger 404 so that the physician's attention will not be diverted between separate controls of either (e.g. compare FIGS. 11 and 12 with FIG. 1). Thus, the attending physician can concentrate his efforts on the viewing field of the fiberoptic scope without changing his grasp on the needle assembly to accomplish advancement/withdrawal of stylet 416 and aspiration via the syringe.

Since the suction force established by withdrawing plunger 404 in cavity 406 can be quite large, I prefer to incorporate locking structures in the syringe so as to permit the physician to lock the plunger 404 at a predetermined position. To accomplish this function, slots 420, 422 and 424 are defined in plunger 404 and preferably correspond to volumetric displacements in cavity 406 of 5 c.c., 25 c.c. and 30 c.c., respectively, although other volumetric displacements are contemplated. Thus, when plunger 404 is moved to position 430 and is rotated, locking flanges 432, 434 (see FIG. 15) engage in slot 420 so as to lock plunger 404 in position. Similarly, flanges 432, 434 will engage slots 422, 424 when plunger 404 is retracted to positions 440, 442, respectively. The position of the distal end of stylet 416 relative needle 414 and catheter 408 corresponding to plunger positions 430, 440 and 442 are respectively shown in FIG. 14 as "5 c.c.", "25 c.c.", and "30 c.c."; the "0 c.c." being the position of stylet 416 when plunger 404 is completely advanced in cavity 406.

In practice, when utilizing the assembly described above with the Type I fixed needle embodiment, the physician will insert the assembly into the fiberoptic scope with the rounded distal end of the stylet extended beyond the sharp edge of the tubular needle (e.g. the "0 c.c." position shown in FIG. 14). At such position the fiberoptic scope and the patient are protected from inadvertent needle damage. When it is desired to penetrate tissue the stylet is moved to position 430 (e.g. the "5 c.c." position) so as to expose the sharp edge of the needle. At this position the tubular needle is blocked by the stylet therein and thus prevents unwanted tissue from being drawn into the catheter. When sampling is desired, the plunger, and thus stylet, are withdrawn to e.g. the "25 c.c." position (position 440 in FIG. 13) to permit biopsy samples to be drawn into cavity 406 by virtue of the suction created by moving plunger 404 from position 430 to position 440. At each position, the physician can lock the plunger in place as previously described. In the event hard tumors are present in the biopsy material and thus would not readily be transported through the catheter, the physician may introduce a liquid fixative or saline solution into the catheter by dipping the needle therein when removed from the scope and withdrawing the plunger to e.g. the "30 c.c." position. Thereafter, the plunger can be advanced to the "5 c.c." position and such position can be sensed by the physician due to back pressure exerted on the plunger whereupon the syringe can be removed from the catheter by cutting the latter, capped and transported to the laboratory for analysis of the biopsy samples.

With respect to the Type III embodiment, the above procedures are somewhat reordered so that the protective functions will be realized when the stylet is at the "5 c.c." position. Thereafter, to advance the needle into the desired tissue, the stylet is advanced to the "0 c.c." position so as to expose its sharp edge. Thereafter, the procedures described above with respect to the Type I embodiment are followed to obtain the desired tissue samples.

Thus, according to all embodiments of the present invention, the bronchoscope and patient are protected against inadvertent needle damage, yet the attending physician is able to reliably perform the desired tissue biopsy. Accordingly, while the present invention has been herein described in what is presently conceived to be the most preferred embodiments thereof, those in the art may appreciate that many modifications may be made hereof, which modifications shall be accorded the broadest interpretation of the appended claims so as to encompass all equivalent assemblies, structures and/or devices.

What I claim is:

1. A completely flexible bronchoscopic needle assembly for use with a flexible bronchoscope comprising:
   an elongated flexible catheter having proximal and distal ends and defining an interior cavity therebetween;
   a hard tip including means for rigidly fixing a proximal end portion of said tip to said catheter distal end;
   a hollow needle rigidly and coaxially fixed to said tip, said needle including protecting means for protecting the bronchoscope and patient from inadvertent damage, said protecting means defining smoothly rounded surfaces on its distal end away from said tip, the hollow of said needle being in communication with and having a cross-sectional diameter less than said interior cavity;
   tissue penetrating means reciprocably moveable between at least a first advanced position and a second withdrawn position including a flexible stylet defining a sharp edge on its distal end and being of sufficient length to be extendable beyond said rounded surface while in said first position for penetrating tissue when advanced to said first position and permitting said protecting means to protect said bronchoscope and said patient while yet permitting sampling of said tissue when withdrawn to said second position, the diameter of said stylet closely fitting within said hollow of said needle thereby defining with said interior cavity of substantially annular space through which biopsy material can flow;
   cap means fixed to a proximal end of said stylet and engageable with said proximal end of said catheter for coupling said stylet to said catheter thereby locking said stylet in said first extended position, and
   retraction preventing means operatively associated with said tissue penetrating means for preventing retraction of said tissue penetrating means in response to axial compressive forces acting thereon in a direction towards said second position when said tissue penetrating means is in said first position, said retraction preventing means including means defining a spring area integral with said stylet, said integral spring area-defining means of said stylet bearing against said proximal end portion of said hard tip when said stylet is in said first extended position for establishing the limit of said first extended position, said spring area-defining means being flexed against said proximal end portion of said hard tip in response to said cap means being coupled to said catheter to exert a bias force against said proximal end portion of said hard tip thereby biasing said stylet in said first position to resist axial compressive forces acting thereon tending to encourage said stylet to be withdrawn into said needle whereby retraction of said stylet in response to such forces is prevented.

2. An assembly as in claim 1 further comprising means in communication with said annular space for permitting aspiration of said biopsy material therethrough.

3. An assembly as in claim 2 wherein said aspirating means includes:
 syringe means having a syringe body attached to said catheter and defining a syringe cavity in communication with said annular space; and
 a syringe plunger attached to said stylet and being reciprocably moveable in said syringe cavity for simultaneously establishing the position of the distal end of said stylet relative said needle and creating a suction force of predetermined magnitude by the reciprocal manipulation of said syringe plunger in said syringe cavity.

4. An assembly as in claim 3 wherein said aspirating means further includes locking means for locking said plunger in at least one position corresponding to a predetermined volumetric displacement of said syringe plunger in said syringe cavity.

5. An assembly as in claim 4 wherein said locking means includes means defining a plurality of axially separate slots in said plunger, and flange means fixed to said syringe body for engaging a predetermined one of said slots when said plunger is rotated while said predetermined one of said slots and said flange means are registrable with one another to prevent said plunger from being either advanced or withdrawn while in said engaging relationship until such time as said plunger is rotated to disengage said predetermined one of said slots and said flange means to permit reciprocal movement of said syringe plunger in said syringe cavity.

6. In combination with a bronchoscope, the assembly of claim 1.

7. An assembly as in claim 1 wherein said fixing means includes means defining male threads for being threadably engaged with said catheter.

8. A completely flexible bronchoscopic needle assembly for use with a flexible bronchoscope to obtain biopsy tissue samples from a patient, said assembly comprising:
 an elongated flexible outer catheter having proximal and distal ends and defining an outer catheter cavity therebetween, said outer catheter including means defining a bearing surface at said proximal end thereof;
 a hard tip including means for rigidly fixing said tip to said outer catheter distal end;
 a hollow needle slideably and coaxially received in said tip and reciprocably moveable therein between a retracted position whereby said needle is retractably housed within said catheter to prevent inadvertent damage to said bronchoscope or said patient thereby and an extended position whereby said needle is extended beyond the distal surface of said tip to permit the taking biopsy tissue samples, said needle at its distal end defining a sharp edge for penetrating body tissue;
 connecting means connected to said needle for permitting reciprocal movement thereof between said retracted and extended positions; and
 a stylet defining a cutting edge at its distal end slideably received in said hollow of said needle and reciprocably moveable between a first extended position wherein said cutting edge is in advance of said needle and a second retracted position wherein said cutting edge is withdrawn into said needle, said stylet including at its proximal end (a) cap means for coupling said stylet to said outer catheter thereby locking said stylet in said first position, and (b) means defining a spring area integral with said stylet, said integral spring area-defining means for bearing against said bearing surface of said outer catheter and being flexed thereagainst when said cap means is lockably coupled to said outer catheter to exert a bias force aginst said bearing surface thereby biasing said cutting edge into said first extended position to prevent retractable movement of said stylet when in said first extended position when axial compressive forces act upon said stylet in a direction towards said second retracted position.

9. An assembly as in claim 8 wherein said means for effecting reciprocal movement of said needle includes an elongated inner catheter slideably receivable in said outer catheter cavity, said needle being fixed to and carried with the distal end of said inner catheter.

10. A completely flexible bronchoscopic needle assembly for use with a flexible bronchoscope comprising:
 an elongated flexible catheter having proximal and distal ends and defining an interior cavity therebetween;
 a hollow needle coaxially fixed to said catheter distal end, the hollow of said needle being in communication with said interior cavity;
 a flexible stylet slideably received in said interior cavity and being of sufficient length to extend beyond the end of the needle and the proximal end of said catheter, said stylet being reciprocally moveable between an extended position wherein the distal end of the stylet extends beyond the end of the needle and a retracted position wherein the distal end of the stylet is retracted into said catheter;
 means operatively associated with said distal end of said catheter for protecting said bronchoscope and said patient from inadvertent damage while yet permitting penetration of said tissue to obtain samples thereof when desired;
 aspirating means in fluid communication with said inner cavity and connected to said stylet for relatively positioning said stylet in said catheter and for creating a suction source sufficient to transport said tissue samples through said catheter inner cavity so that said tissue samples will be collected for examination;
 locking means operatively associated with said aspirator means for locking said stylet in said extended position;

retraction-preventing means operatively associated with said stylet for preventing retraction of said stylet in response to axial compressive forces acting thereon in a direction towards said retracted position when said stylet is in said extended position, said retraction-preventing means including (a) means defining a bearing surface, and (b) means defining a spring area integral with said stylet, said spring area-defining means for bearing against said bearing surface to be flexed thereagainst in response to said locking means locking said stylet in said extended position to exert a bias force against said bearing surface thereby biasing said stylet into said first position to resist axial compressive forces acting thereon tending to encourage said stylet to be withdrawn into said needle, whereby retraction of said stylet in response to said compressive forces is prevented.

11. An assembly as in claim 10 wherein said aspirating means includes syringe means having a syringe body attached to said catheter and defining a syringe cavity in communication with said inner cavity, and a syringe plunger attached to said stylet and being reciprocably moveable in said syringe cavity for simultaneously establishing the position of the distal end of said stylet relative said needle and for creating a suction force of predetermined magnitude by the reciprocal manipulation of said syringe plunger in said syringe cavity.

12. An assembly as in claim 11 wherein said locking means locks said plunger in at least one position corresponding to a predetermined volumetric displacement of said syringe plunger in said syringe cavity.

13. An assembly as in claim 12 wherein said locking means includes means defining a plurality of axially separated slots in said plunger, and flange means fixed to said syringe body for engaging a predetermined one of said slots when said plunger is rotated while said predetermined one of said slots and said flange means are registrable with one another to prevent said plunger from being either advanced or withdrawn while in said engaging relationship until such time as said plunger is rotated to disengage said predetermined one of said slots and said flange means to permit reciprocal movement of said syringe plunger in said syringe cavity.

* * * * *